United States Patent
Zhang et al.

(10) Patent No.: US 10,066,243 B2
(45) Date of Patent: Sep. 4, 2018

(54) SURFACTANT IMPROVED ETHANOL FERMENTATION METHOD

(71) Applicant: DALIAN INSTITUTE OF CHEMICAL PHYSICS, CHINESE ACADEMY OF SCIENCES, Dalian (CN)

(72) Inventors: Zongchao Zhang, Dalian (CN); Xiumei Liu, Dalian (CN)

(73) Assignee: DALIAN INSTITUTE OF CHEMICAL PHYSICS, CHINESE ACADEMY OF SCIENCES, Dalian (CN)

(*) Notice: Subject to any disclaimer, the term of this patent is extended or adjusted under 35 U.S.C. 154(b) by 4 days.

(21) Appl. No.: 14/909,801

(22) PCT Filed: Apr. 14, 2014

(86) PCT No.: PCT/CN2014/000398
§ 371 (c)(1),
(2) Date: Feb. 3, 2016

(87) PCT Pub. No.: WO2015/035734
PCT Pub. Date: Mar. 19, 2015

(65) Prior Publication Data
US 2016/0194668 A1    Jul. 7, 2016

(30) Foreign Application Priority Data

Sep. 12, 2013 (CN) .......................... 2013 1 0416058
Dec. 9, 2013 (CN) .......................... 2013 1 0660369

(51) Int. Cl.
*C12N 1/00* (2006.01)
*C12P 7/06* (2006.01)
*C12N 1/38* (2006.01)

(52) U.S. Cl.
CPC .................. *C12P 7/06* (2013.01); *C12N 1/38* (2013.01); *Y02E 50/17* (2013.01)

(58) Field of Classification Search
None
See application file for complete search history.

(56) References Cited

U.S. PATENT DOCUMENTS

| | | | |
|---|---|---|---|
| 2010/0143993 A1 | 6/2010 | Erdner-Tindall | |
| 2011/0171707 A1* | 7/2011 | Holt .......................... | C12N 1/18 435/161 |
| 2011/0201093 A1 | 8/2011 | Czechowski et al. | |
| 2011/0319454 A1* | 12/2011 | Beard ..................... | A61K 31/16 514/352 |

FOREIGN PATENT DOCUMENTS

WO    2010/065595 A2    6/2010

OTHER PUBLICATIONS

Pereira et al. Biotechnol. Lett. (2012) 34: 45-53.*
English translation of Song et al. J. Zhangzhou University Light Industry (Natural Science) (2006) 21(4): 18-20.*
Thomas et al. Applied Environmental Microbiol. (1994) 60(5): 1519-1524.*
Larsson et al. J. Microb. Biotech. (1988) 3(2): 22-29.*
Definition of "polymer" downloaded from thefreedctionary.com/polymer webpage on Sep. 9, 2017.*
Schink et al. Appl. Environ. Microbiol. (1983) 45(6): 1905-1913 (Year: 1983).*
Zhang et al. Biotechnol. Bioprocess Engineering (2011) 16: 930-936 (Year: 2011).*
Bai, F.W. et al., Parameter Oscillations in a Very High Gravity Medium Continuous Ethanol Fermentation and Biotechnology and Their Attenuation on a Multistage Packed Column Bioreactor System, Biotechnology and Bioengineering, vol. 88, No. 5, Oct. 6, 2014, pp. 558-566.
Song, Andong et al., Research on Optimum of Fermentation System during Co-fermentation of Pentose and Hexose to Fuel Ethanol, Journal of Zhengzhou University of Light Industry (Natural Science), vol. 2, No. 4, Nov. 30, 2006, pp. 18-20 (English abstract is included).
Hu, Chunkeng., Medium Optimization for and yeast physiology changes during very high gravity ethanol fermentation, Chemical Industry and Engineering Progress, vol. 29, Dec. 20, 2010, pp. 300-304(English abstract is included).
Min Enze, "Developing Bioref inery by Utilizing Agriculture and Forestry Biomass Resources : Striding Forward the'Carbohydrate' Era", Progress in Chemistry, 2006, 18(2-3): 131-141(English abstract is included).
Kwang Ho Lee, et al. ((Bioresource Technology, 102, 2011: 8191-8198).
Yue et al., "The influence of nitrogen sources on ethanol production by yeast from concentrated sweet sorghum juice", Biomass and Bioenergy 39, 2012:48-52.
Deesuth et al., "Optimization of Nitrogen and Metal Ions Supplementation for Very High Gravity Bioethanol Fermentation from Sweet Sorghum Juice Using an Orthogonal Array Design" Energies 2012, 5, 3178-3197.

* cited by examiner

*Primary Examiner* — Susan M Hanley
(74) *Attorney, Agent, or Firm* — Enshan Hong; VLP Law Group LLP

(57) ABSTRACT

A surfactant-improved ethanol fermentation method comprises adding a nonionic surfactant as a protection agent of yeast cell into a fermentation culture medium, therefore greatly improving survival rate of yeast cells in very high gravity ethanol fermentation liquid and endpoint ethanol concentration. The present invention not only improves the cyclic utilization efficiency of the yeast cells, but also achieves the synchronous recycling of the surfactant and a pH adjusting agent. The process of adding the surfactant during VHG fermentation is simple, which can reduce the consumption of water and energy, effectively reduce the fuel ethanol production cost, and improve the fermentation efficiency.

17 Claims, 9 Drawing Sheets

SURFACTANT IMPROVED ETHANOL FERMENTATION METHOD

PRIORITY CLAIM

This is a U.S. national stage of application No. PCT/CN2014/000398 filed on Apr. 14, 2014, which claims priority from China Patent Application Nos. 201310416058.X filed Sep. 12, 2013 and 201310660369.0 filed Dec. 9, 2013, the entire content of which is incorporated herein as reference.

FIELD OF THE INVENTION

The present invention relates to the field of ethanol production through a fermentation process, in particular to a surfactant-improved ethanol fermentation method under VHG fermentation conditions.

BACKGROUND OF THE INVENTION

With the rapid development of world economy, the degree of dependence of people on fossil resources is gradually increased. The high-strength mining and consumption of the fossil resources cause emission of a great amount of harmful gases such as $CO_2$ (Progress in Chemistry, 2006, 18(2-3): 131-141), which consequently leads to serious environmental pollution and influences the existence and development of the human society. In recent years, in order to relieve the increasing shortage of energy and the crisis of global environmental temperature rise caused by the increase of greenhouse gas emission, people are successively devoted in developing "green" alternative energy. As new renewable energy, fuel ethanol has the features of cleanness, renewability and the like, can reduce the emission of carbon monoxide and hydrocarbon in automobile exhaust, and is one of major countermeasures for effectively relieving the energy crisis.

The production of bioethanol is mainly to convert various biomasses into fuel ethanol through microbial fermentation. Reducing the production cost is a key factor for improving the economic benefit of production of fuel ethanol, especially cellulosic ethanol, and enabling it to be widely applied. In order to effectively reduce the production cost, currently people are mainly devoted in improving the fermentation time, improving the cyclic utilization efficiency of yeast and improving the endpoint ethanol concentration. Kwang Ho Lee, et al. ((Bioresource Technology, 102, 2011: 8191-8198) reported a method for immobilizing yeast by using calcium alginate as a carrier. Compared with free cells, immobilized yeast can obtain higher ethanol yield and can effectively shorten the fermentation time by 10 h; U.S. patent US20110201093A1 reports that the ethanol yield can be improved and the fermentation time can be reduced by adding carbonate into the fermentation medium; and the patents US20100143993A1 and WO2010/065595A2 adopt ionic liquid as an extraction agent to continuously extract ethanol in situ from the fermentation system to guarantee the activity of yeast.

Very high gravity (VHG) fermentation is a technique capable of improving the economic indicator of ethanol fermentation. The VHG ethanol fermentation has the following advantages: 1) the productivity and utilization rate of unit equipment are improved; 2) water consumption is reduced; 3) the ethanol in mash in unit volume is increased, and the energy consumption in cooking, fermentation, distillation and DDGS concentration and drying processes is reduced; and 4) the growth of contaminating microorganisms is inhibited. However, VHG ethanol fermentation also causes some problems for a reason that the starting sugar concentration is obviously increased. On one hand, since the yeast cells are stressed by high osmotic pressure under the effect of high sugar concentration, consequently the growth and survival rate are decreased, the fermentation time is prolonged and the fermentation is incomplete; on the other hand, the yeast cells are inhibited by strong products of high-concentration ethanol; the fermentation is also inhibited by nutrient insufficiency. The literatures (Biomass and Bioenergy 39, 2012:48-52) and (Energies 2012, 5, 3178-3197) discussed about improving the endpoint ethanol concentration by adding different types of nitrogen sources under VHG ethanol fermentation conditions.

The present invention discloses a surfactant-improved ethanol fermentation method, wherein high-activity *saccharomyces cerevisiae* is adopted, glucose is used as a raw material, a nonionic surfactant is added during fermentation cultivation to reduce ethanol inhibition, thereby the osmotic pressure caused by high sugar concentration is reduced, the survival rate and growth speed of the *saccharomyces cerevisiae* cells under special environments are improved, finally the endpoint ethanol concentration is improved and the consumption of water in the fermentation process and the consumption of energy in the distillation process are effectively reduced; and in addition, the yeast and the surfactant are separated from the fermentation mixture and then are reutilized in the next batch of fermentation processes.

SUMMARY OF THE INVENTION

The purpose of the invention is to provide a surfactant-improved ethanol fermentation method and relates to a very high gravity (VHG) fermentation ethanol production process, in particular to surfactant-improved VHG ethanol fermentation, wherein endpoint ethanol concentration is improved by adding a surfactant in a fermentation medium. It is well known that fuel ethanol is produced mainly through a fermentation method, the fermentation medium comprises carbohydrate, a sugar source and *saccharomyces cerevisiae*, the initial pH of the fermentation medium is 3.5-5.3 and the fermentation temperature is 25-40° C. The invention is directed to adding a nonionic surfactant into the fermentation medium to improve the ethanol concentration and the survival ability of yeast cells, and the ethanol can be increased from 110 g/L when no surfactant is added to 150 g/L when the surfactant is added.

The present invention provides a surfactant-improved ethanol fermentation method, wherein a fermentable carbohydrate is used as a carbon source, a surfactant-water mixture is used as a fermentation medium, a pH adjusting agent is added to adjust the pH value of the fermentation medium and the *saccharomyces cerevisiae* cells are inoculated to perform very high gravity ethanol fermentation.

According to the surfactant-improved ethanol fermentation method provided by the present invention, the fermentable carbohydrate is glucose and the concentration of the fermentable carbohydrate is 270-500 g/L.

According to the surfactant-improved ethanol fermentation method provided by the present invention, a mass ratio of the surfactant to water in the fermentation medium is 0.001-0.5, preferably 0.125-0.375.

According to one embodiment of the present invention, the surfactant-improved ethanol fermentation method comprises that: (a) the fermentation medium comprises *saccha-*

*romyces cerevisiae*; (b) the fermentation medium therein comprises at least one of such nonionic surfactants as polyethylene glycol (PEG), methoxy polyethylene glycol (MPEG), dimethoxy polyethylene glycol (DMPEG) and polydimethylsiloxane (PDMS), and the addition of the surfactant can increase the life of yeast cells and endpoint ethanol concentration under VHG fermentation conditions; (c) the yeast cells can be recycled from the fermentation mixture; and (d) the surfactant and the pH adjusting agent can be synchronously recycled.

The PEG is at least one of PEG-200, 400, 600, 800, 1000. A structural formula of the PEG is:

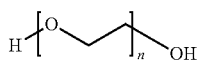

a structural formula of the MPEG is:

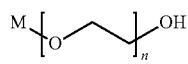

a structural formula of the DMPEG is:

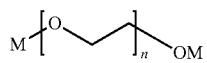

and a structural formula of the PDMS is:

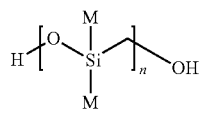

wherein n is 1-25; and M is alkyl.

According to the present invention, a fermentation process or at least part of the fermentation process comprises the fermentation medium $H_2O$ and surfactant, a fermentation product ethanol, a fermentation material carbohydrate and *saccharomyces cerevisiae*. In one embodiment, the fermentation temperature is generally selected to be 28-44° C., in particular 30-38° C., the most preferably 33° C., the pH is generally selected to be 3.0-6.5, the most preferable pH range is 4.0-5.0, the yeast cell concentration is $10^7$-$10^9$/L, and the fermentation time is 12-120 hrs, preferably 60 hrs.

According to the surfactant-improved ethanol fermentation method provided by the present invention, the pH adjusting agent for the fermentation medium is one of sulfuric acid solution, citric acid-sodium citrate buffer solution, phosphoric acid buffer solution, carbonate buffer solution and acetic acid-sodium acetate buffer solution.

In the VHG fermentation process, the bearing capacity of the yeast cells to the osmotic pressure of high-concentrating glucose and the tolerance to high-concentration ethanol are key factors that need to be considered. In the present invention, the ethanol concentration can be effectively improved by adding the nonionic surfactant into the fermentation medium. We guess that this phenomenon is caused possibly for a reason that the surfactant is directly or indirectly used as a cell protection agent which improves the survival ability of the yeast cells and thereby improves the ethanol concentration.

The used surfactant is a nonionic surfactant, for example, the nonionic surfactant is PEG, in particular PEG-200, PEG-400 and PEG-600. The mass ratio of the surfactant to water is 0 to 2/3, the mixed fermentation medium of the surfactant and the water can increase the ethanol concentration, which is consistent with the point of view put forward by the present invention. The fermentation medium prepared by mixing according to a mass ratio of surfactant to water between 1/5 and 2/3 and between 1/5 and 1/4 can also increase the ethanol concentration.

A fermentation bath for ethanol production provided by the present invention comprises microorganisms (such as yeast) for producing ethanol, a fermentation carbon source (such as carbohydrate, monosaccharide and polysaccharide) and a pH adjusting agent (such as $H_2SO_4$, citric acid-sodium citrate buffer solution, phosphoric acid buffer solution, carbonate buffer solution and acetic acid-sodium acetate buffer solution). The concentration of a fermentation substrate is 275-500 g/L, the fermentation substrate consists of a fermentable carbohydrate, and glucose, cellulose and starch are especially suitable as the carbon source.

According to the surfactant-improved ethanol fermentation method provided by the present invention, the yeast cells can be recycled and are recovered by performing refrigerated centrifugation to the fermentation liquid for direct use in the next fermentation process. The yeast cells are recycled by performing refrigerated centrifugation to the fermentation liquid by adopting a standard centrifugation technique with a centrifugation speed of 4000-15000 rpm and a centrifugation time of 1-30 min.

According to the surfactant-improved ethanol fermentation method provided by the present invention, the surfactant and the pH adjusting agent can be recycled, refrigerated centrifugation is performed to remove the yeast and supernatant is distilled to obtain residue which replaces a fresh surfactant for a next fermentation process. The surfactant and the pH adjusting agent are recovered by adopting a standard vacuum distillation technique, distillation temperature under pressure of 0-0.09 Mpa is 40-100° C. and distillation time is 20-120 min.

According to the surfactant-improved ethanol fermentation method provided by the present invention, the yeast cells and the surfactant can be synchronously recycled, the yeast cells are recovered through refrigerated centrifugation, the supernatant is distilled to recover the surfactant, and the recovered yeast cells and the recovered surfactant are simultaneously used for a next batch of fermentation processes.

According to the surfactant-improved ethanol fermentation method provided by the present invention, the surfactant is recycled by performing refrigerated centrifugation after fermentation to remove the yeast cells, recovering the surfactant and the pH adjusting agent through a standard vacuum distillation technique, the fermentable carbohydrate, the deionized water and the recovered surfactant and pH adjusting agent can be directly added in the next fermentation process, and the pH value of the fermentation medium does not need to be adjusted again.

The surfactant not only is low in steam pressure, but also has adjustable water solubility, and a fine regulation and control of the physical property thereof can be realized by selecting its structure and the molecular weight. This series of features decide that the surfactant has wide biocompatibility to many microorganisms and can be separated from the fermentation mixture by adopting techniques such as centrifugation and distillation. A yeast cell recovery process provided by the present invention is that the yeast cells can be recycled from the fermentation mixture of the surfactant and the water through centrifugal separation. Specific process steps are as shown in FIG. 1.

In one embodiment, the present invention provides a surfactant recovery process: the surfactant can be recycled from the fermentation mixture through the standard distillation technique after fermentation and the surfactant can be cyclically utilized. Specific process steps are as shown in FIG. 2.

Material and Fermentation Analysis Process

*Saccharomyces cerevisiae* was obtained from Hubei Angel Yeast Co., Ltd. Other reagents and chemicals were obtained from SINOPHARM GROUP. Firstly, a certain amount of *saccharomyces cerevisiae* was weighed and put in a 100 mL conical flask, rehydrated to activate for 20 min at 37° C. by using ultrapure water, and then the resulting solution could be used as yeast broth. Then glucose, surfactant and pre-prepared solution with a certain pH value were added in the conical flask to be sealed by a preservative film, the conical flask was put in a shaker for shaking culture, and the revolving speed of shaker was 160 r/min.

After fermentation, a product sample was diluted by deionized water, the content of each component in the fermentation liquid was determined by adopting high performance liquid chromatograph (Agilent 1260), the conversion rate and the ethanol yield thereof were calculated according to the feeding amount of the glucose, and the ethanol concentration was calculated according to the mass of ethanol in the fermentation liquid and the volume of activated water and pH solution. Chromatographic conditions are: ion exchange column with the column temperature of 65° C., differential refraction detector with detector temperature of 50° C.; and mobile phase: 5 Mm $H_2SO_4$, flow rate of 0.6 ml/min and inlet amount of 25 uL.

$$\text{Glucose conversion rate} = \frac{\left(\begin{array}{c}\text{glucose feeding amount (mol)} - \\ \text{glucose residual amount (mol)}\end{array}\right)}{\text{glucose feeding amount (mol)}} \times 100\%$$

$$\text{Ethanol yield} = \frac{\text{actual produced ethanol amount (mol)}}{2 * \text{glucose feeding amount (mol)}} \times 100\%$$

$$\text{Ethanol concentration (g/L)} = \frac{\text{actual produced ethanol amount (g)}}{H2O(L)}$$

DESCRIPTION OF THE EMBODIMENTS

Figure 1:
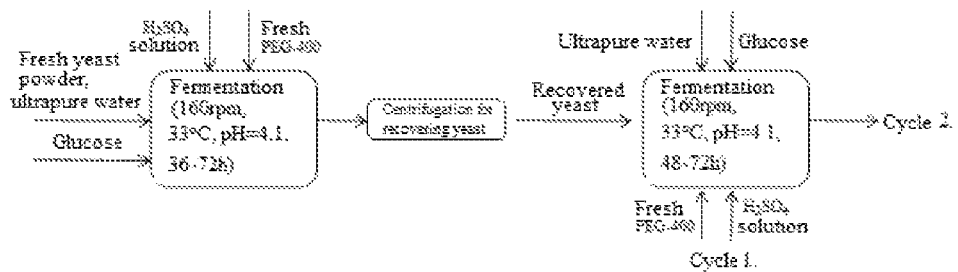
FIG. 1 illustrates recycling process steps of solid yeast powder.
Figure 2:
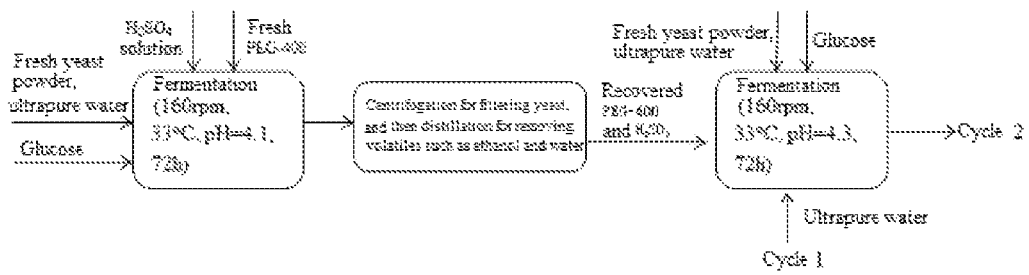
FIG. 2 illustrates synchronous recycling process steps of the surfactant and sulfuric acid.

The present invention will be further described below in combination with specific examples. However, the claimed scope of the present invention is not limited by the examples. Non-substantive improvement and adjustment made to the present invention by one skilled in the art according to the above-mentioned contents of the present invention shall also belong to the claimed scope of the present invention.

Examples 1-9 Influences of the Ratio of PEG-200 to Water on Ethanol Fermentation Efficiency Firstly, 0.4 g of *saccharomyces cerevisiae* was weighed and put in a 100 mL conical flask, rehydrated to activate for 20 min at 38° C. by using 4 mL of ultrapure water, and then the resulting solution could be used as yeast broth. Then 6.0 g of glucose, PEG-200 (according to the amount in Table 1) (1-8 g) and pre-prepared $H_2SO_4$ solution with pH=3.4 (according to the amount in Table 1) were added, the conical flask was sealed by a preservative film, put in a shaker for shaking culture for 48 hrs at 36° C., and the revolving speed of shaker was 160 r/min. According to the data in Table 1, it can be seen that, when no PEG-200 was added into the fermentation system (example 1), the glucose conversion rate was 96%, the ethanol yield was 81% and the ethanol concentration was 112 g·L$^{-1}$; and when 1.0 g of PEG-200 was used to replace pH solution, the glucose conversion rate was increased to 99%, the ethanol yield was increased to 88%, the ethanol concentration was increased to 129 g·L$^{-1}$, and the glucose conversion rate, the ethanol yield and the ethanol concentration firstly ascended and then dropped with the increase in the amount of the PEG-200. These results preliminarily demonstrate that the PEG can replace the water as the fermentation medium within a certain ratio range, improve the concentration of the fermentation endpoint product ethanol, reduce the content of residual glucose at the fermentation endpoint, reduce the consumption of the water, decrease the production cost and improve the fermentation efficiency.

TABLE 1

Influences of the ratio of PEG-200 to water on ethanol fermentation efficiency

| Example | PEG-200/g | $H_2O$/mL | Mass ratio of PEG to $H_2O$ | Glucose conversion rate/% | Ethanol yield/% | Ethanol concentration/ $g \cdot L^{-1}$ |
|---|---|---|---|---|---|---|
| 1 | 0 | 20 | 0 | 96 | 81 | 112 |
| 2 | 1.0 | 19 | 1/19 | 99.4 | 88.2 | 129.3 |
| 3 | 2.0 | 18 | 2/18 | 93.8 | 86.5 | 133.8 |
| 4 | 3.0 | 17 | 3/17 | 81.4 | 78.6 | 128.7 |
| 5 | 4.0 | 16 | 4/16 | 71.3 | 71.8 | 125.0 |
| 6 | 5.0 | 15 | 5/15 | 48.1 | 45.8 | 85.1 |
| 7 | 6.0 | 14 | 6/14 | 24.9 | 21.9 | 43.6 |
| 8 | 7.0 | 13 | 7/13 | 12.5 | 14.0 | 30.0 |
| 9 | 8.0 | 12 | 8/12 | 5.5 | 9.3 | 21.5 |

Examples 10-17 Influences of the Ratio of PEG-400 to Water on Ethanol Fermentation Efficiency 0.4 g of yeast was weighed and put in a 100 mL conical flask, rehydrated to activate for 20 min at 38° C. by using 4 mL of ultrapure water, and then the resulting solution could be used as yeast broth. Then 6.0 g of glucose, PEG-400 (according to the amount in Table 2) (1-8 g) and pre-prepared $H_2SO_4$ solution with pH=3.4 (according to the amount in Table 2) were added, the conical flask was sealed by a preservative film, and put in a shaker for shaking culture for 48 hrs at 36° C., and the revolving speed of shaker was 160 r/min. According to the data in Table 2, it can be seen that, when 4.0 g of PEG-400 was used to replace pH solution, the ethanol concentration could reach to 150 $g \cdot L^{-1}$, and almost no glucose was remained in the fermentation system. These results further proved that the PEG can replace the water as the fermentation medium within a certain ratio range, improve the concentration of the fermentation endpoint product ethanol, reduce the content of the residual glucose at the fermentation endpoint, reduce the consumption of the water, decrease the production cost and improve the fermentation efficiency.

TABLE 2

Influences of the ratio of PEG-400 to water on ethanol fermentation efficiency

| Example | PEG-400/g | $H_2O$/mL | Mass ratio of PEG to $H_2O$ | Glucose conversion rate/% | Ethanol yield/% | Ethanol concentration/ $g \cdot L^{-1}$ |
|---|---|---|---|---|---|---|
| 1 | 0 | 20 | 0 | 96 | 81 | 112 |
| 10 | 1.0 | 19 | 1/19 | 99.4 | 88.1 | 129.3 |
| 11 | 2.0 | 18 | 2/18 | 99.1 | 90.0 | 139.4 |
| 12 | 3.0 | 17 | 3/17 | 99.5 | 89.3 | 146.5 |
| 13 | 4.0 | 16 | 4/16 | 99.3 | 86.8 | 151.3 |
| 14 | 5.0 | 15 | 5/15 | 93.9 | 79.6 | 148.0 |
| 15 | 6.0 | 14 | 6/14 | 84.3 | 69.6 | 138.7 |
| 16 | 7.0 | 13 | 7/13 | 43.0 | 26.0 | 55.7 |
| 17 | 8.0 | 12 | 8/12 | 19.6 | 4.0 | 9.3 |

Examples 18-25 Influences of the Ratio of PEG-600 to Water on Ethanol Fermentation Efficiency 0.4 g of yeast was weighed and put in a 100 mL conical flask, rehydrated to activate for 20 min at 38° C. by using 4 mL of ultrapure water, and then the resulting solution could be used as yeast broth. Then 6.0 g of glucose, PEG-600 (according to the amount in Table 3) (1-8 g) and pre-prepared $H_2SO_4$ with pH=3.4 (according to the amount in Table 3) were added, the conical flask was sealed by a preservative film, and put in a shaker for shaking culture for 48 hrs at 36° C., and the revolving speed of shaker was 160 r/min. According to the data in Table 3, it can be seen that, when PEG-600 was used to replace pH solution, the ethanol concentration gradually ascended and then dropped with the increase in the amount of the PEG-600, and the maximum ethanol concentration could reach to 153 $g \cdot L^{-1}$. These results fully proved that the PEG can replace the water as the fermentation medium within a certain ratio range, improve the concentration of the fermentation endpoint product ethanol, reduce the content of residual glucose at the fermentation endpoint, reduce the consumption of the water, decrease the production cost and improve the fermentation efficiency.

TABLE 3

Influences of the ratio of PEG-600 to pH solution on ethanol fermentation efficiency

| Example | PEG-600/g | $H_2O$/ml | Mass ratio of PEG to $H_2O$ | Glucose conversion rate/% | Ethanol Yield/% | Ethanol concentration/ $g \cdot L^{-1}$ |
|---|---|---|---|---|---|---|
| 1 | 0 | 20 | 0 | 96 | 81 | 112 |
| 18 | 1.0 | 19 | 1/19 | 97.8 | 89.9 | 131.9 |
| 19 | 2.0 | 18 | 2/18 | 97.3 | 90.6 | 140.3 |
| 20 | 3.0 | 17 | 3/17 | 95.4 | 87.9 | 144.1 |
| 21 | 4.0 | 16 | 4/16 | 96.4 | 86.9 | 151.4 |
| 22 | 5.0 | 15 | 5/15 | 89.7 | 81.9 | 152.1 |
| 23 | 6.0 | 14 | 6/14 | 83.3 | 77.3 | 153.7 |
| 24 | 7.0 | 13 | 7/13 | 41.8 | 38.0 | 81.5 |
| 25 | 8.0 | 12 | 8/12 | 10.1 | 6.3 | 14.6 |

Figure 3:
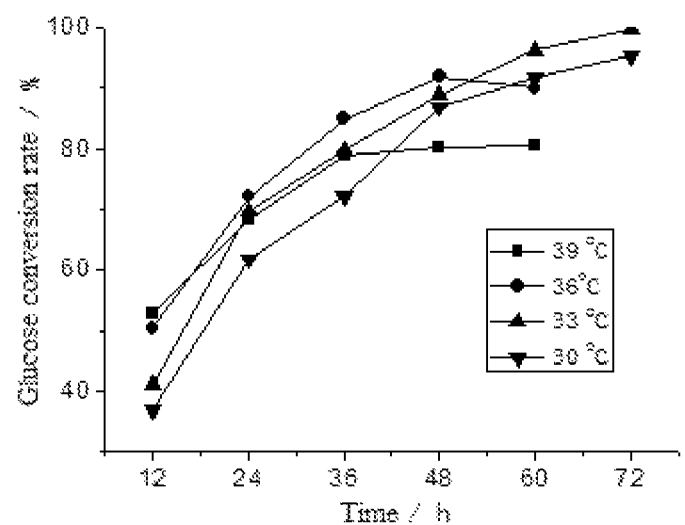
FIG. 3 illustrates the influences of fermentation temperature on glucose conversion rate.
Figure 4:
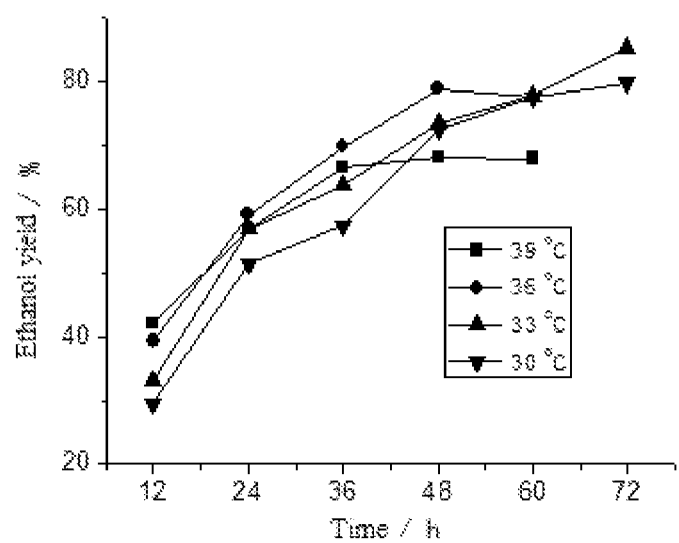
FIG. 4 illustrates the influences of fermentation temperature on ethanol yield.
Figure 5:
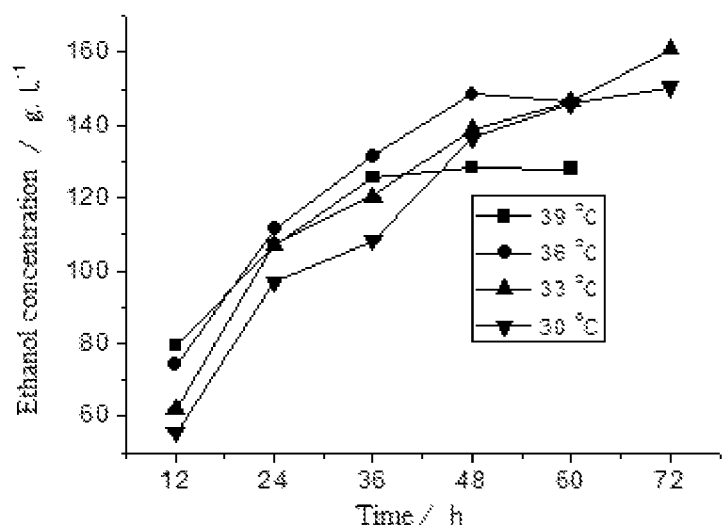
FIG. 5 illustrates the influences of fermentation temperature on ethanol concentration.

Example 26 Influences of Fermentation Temperature 0.5 g of yeast was weighed and put in a 100 mL conical flask, rehydrated to activate for 20 min at 38° C. by using 4 mL of ultrapure water, and then the solution could be used as yeast broth. Then 6.5 g of glucose, 4.0 g of PEG-400 and 12 mL of $H_2SO_4$ solution with pH=3.4 were added, the conical flask was sealed by a preservative film, and put in a shaker for shaking culture for 12-72 hrs at 32-42° C., and the revolving speed of shaker was 160 r/min. According to FIGS. 3, 4 and 5, it can be seen that different temperatures caused the glucose conversion rate, the ethanol yield and the ethanol concentration to be greatly different in the fermentation process, and the endpoint ethanol concentration dropped with the rise of the temperature when the fermentation temperature exceeded 35° C.; and however, the endpoint ethanol concentration also dropped when the temperature dropped to 30° C. The optimum fermentation temperature should be selected to be close to 33° C., the maximum fermentation endpoint ethanol concentration could reach to 160 $g \cdot L^{-1}$ and no residual glucose existed in the fermentation system.

Figure 6:
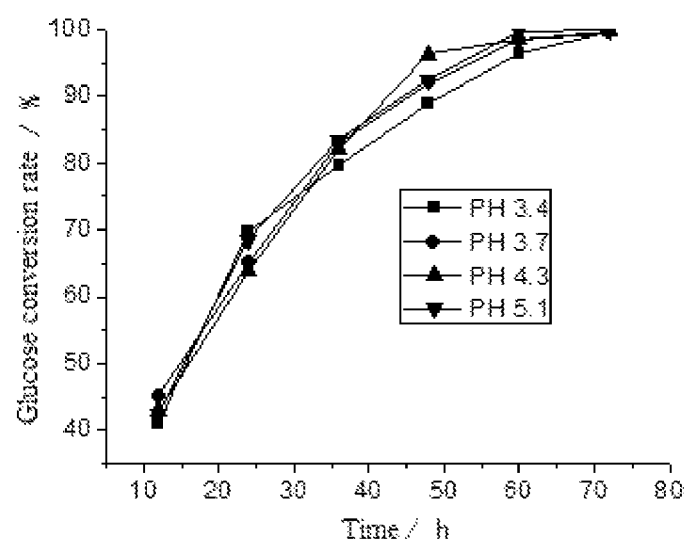
FIG. 6 illustrates the influences of pH value on glucose conversion rate.
Figure 7:
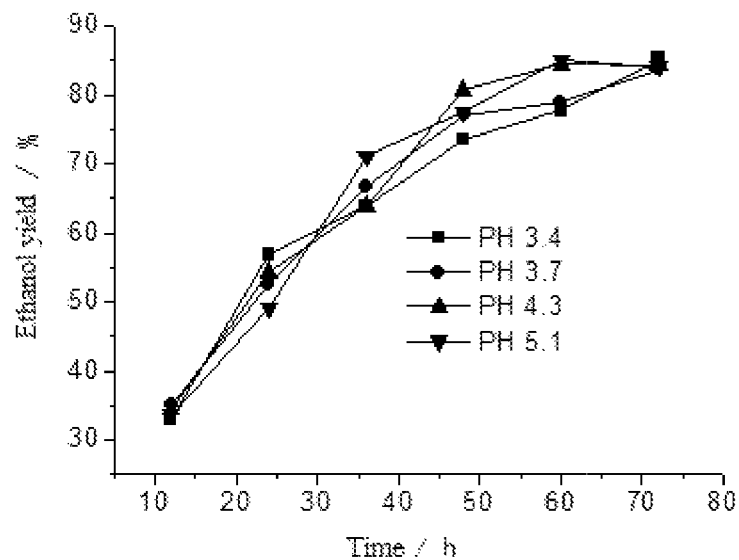
FIG. 7 illustrates the influences of pH value on ethanol yield.
Figure 8:
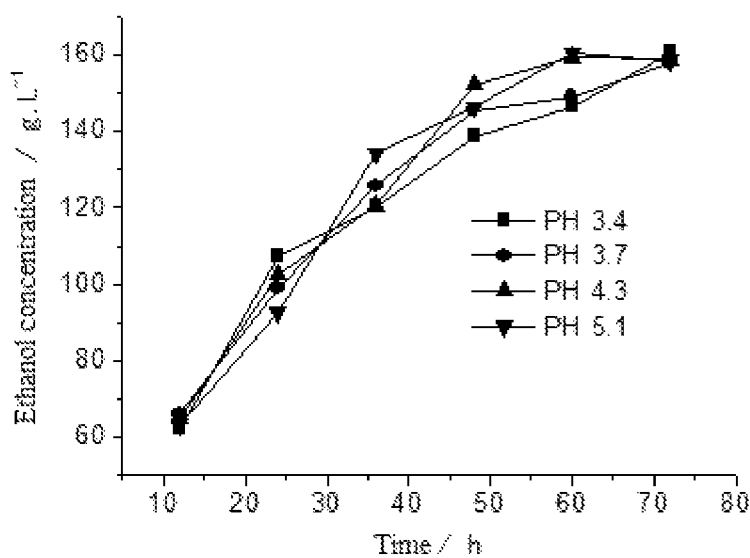
FIG. 8 illustrates the influences of pH value on ethanol concentration.

Example 27 Influences of Fermentation pH 0.5 g of yeast was weighed and put in a 100 mL conical flask, rehydrated to activate for 20 min at 37° C. by using 4 mL of ultrapure water, and then the resulting solution could be used as yeast broth. Then 6.5 g of glucose, 4.0 g of PEG-400 and 12 mL of $H_2SO_4$ solution with pH=3.4-5.1 were added, the conical flask was sealed by a preservative film, and put in a shaker for shaking culture for 12-72 hrs at 35° C., and the revolving speed of shaker was 160 r/min. Since the pH value would influence the permeability of yeast cells and further influence the nutrient substance absorption and ethanol excretion of the yeast cells, suitable pH is critically important to the influence on fermentation. According to FIGS. 6, 7 and 8, it can be seen that, when the pH value of the fermentation liquid is within a range of 4.3-5.1, a fermentation endpoint can be achieved after 60 hrs, the maximum endpoint ethanol concentration can reach to 160 g·L$^{-1}$ and the glucose is fully fermented.

Figure 9:
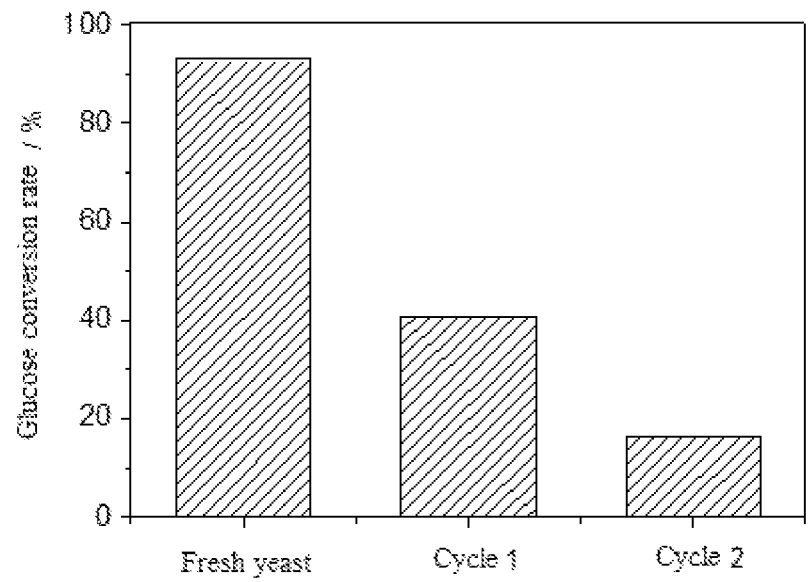
FIG. 9 illustrates the influences of a circulation of yeast fermented for 48 hrs in pure water on glucose conversion rate.
Figure 10:
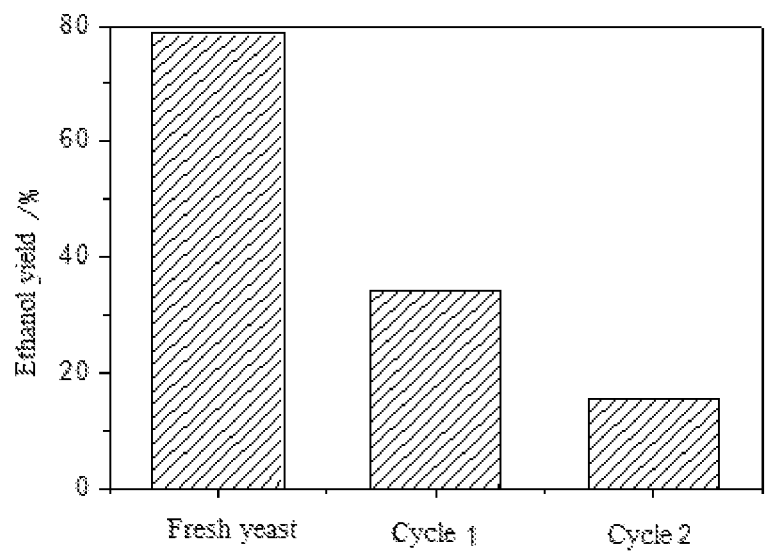
FIG. 10 illustrates the influences of a circulation of yeast fermented for 48 hrs in pure water on ethanol yield.
Figure 11:
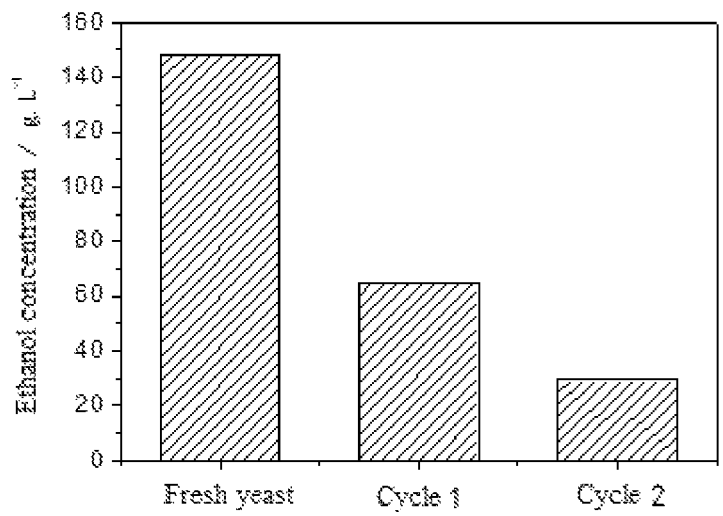
FIG. 11 illustrates the influences of a circulation of yeast fermented for 48 hrs in pure water on ethanol concentration.

Example 28 Recycling of Yeast Fermented for 48 Hrs in Pure Water 0.5 g of yeast powder was rehydrated for 15-30 min at 25-38° C. by using 4 mL of ultrapure water, then 6.5 g of glucose, 12 mL of pre-prepared sulfuric acid solution with pH of 4.3 were added, then and put in a shaker for shaking and fermented for 48 hrs at 33° C. After fermentation, refrigerated centrifugal separation at 8000 rpm was performed for 5 min, the supernatant was removed from the fermentation liquid after fermentation, solid yeast powder was left, 4 mL of ultrapure water, 6.5 g of glucose and 12 mL of sulfuric acid solution were added again, fermented for 48-72 hrs at 33° C., and the above operations were cyclically performed twice. The glucose conversion rate, the ethanol yield and the ethanol concentration are respectively as shown in FIGS. 9, 10 and 11. According to the data in the drawings, it can be seen that, when no surfactant was added into the fermentation system, the recovery efficiency of the yeast was very low and the ethanol concentration of only 60 g·L$^{-1}$ could be achieved at the first time of recycling the recovered yeast after fermentation for 48 hrs.

Figure 12:
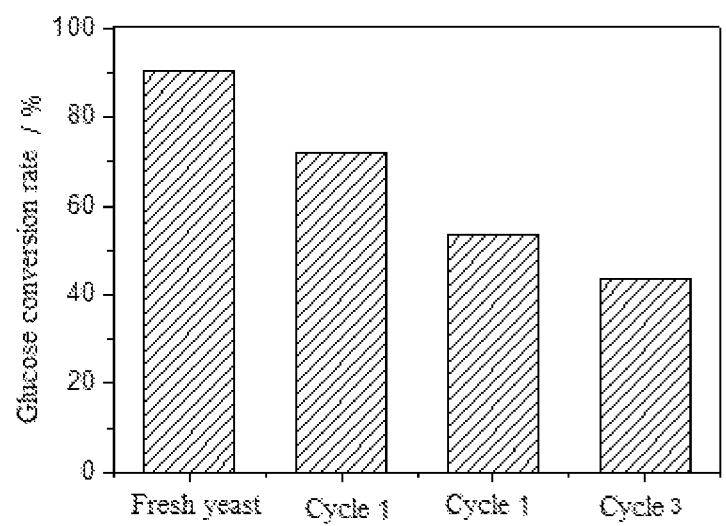
FIG. 12 illustrates the influences of a circulation of yeast fermented for 48 hrs in surfactant/water on glucose conversion rate.
Figure 13:
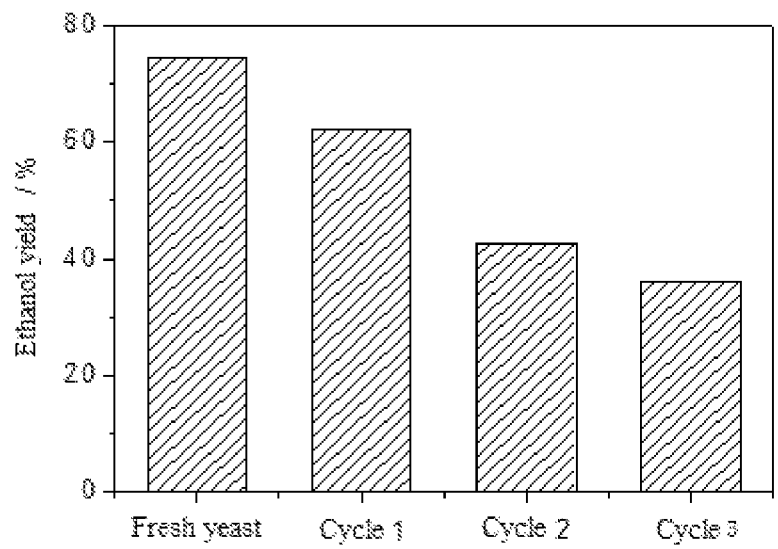
FIG. 13 illustrates the influences of a circulation of yeast fermented for 48 hrs in surfactant/water on ethanol yield.
Figure 14:
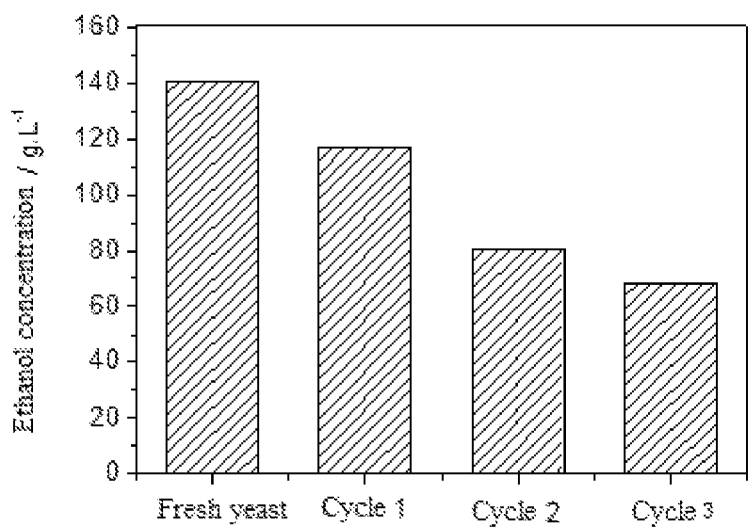
FIG. 14 illustrates the influences of a circulation of yeast fermented for 48 hrs in surfactant/water on ethanol concentration.

Example 29 Recycling of Yeast Fermented for 48 Hrs in Surfactant-Water Mixture System 0.5 g of yeast powder was rehydrated for 15-30 min at 25-38° C. by using 4 mL of ultrapure water, then 6.5 g of glucose, 4.0 g of PEG-400 and 12 mL of pre-prepared sulfuric acid solution with pH of 4.3 were added, then and put in a shaker for shaking and fermentation was performed for 48 hrs at 33° C. After fermentation, refrigerated centrifugal separation at 8000 rpm was performed for 5 min, the supernatant was removed from the fermentation liquid after fermentation, solid yeast powder was left, 4 mL of ultrapure water, 6.5 g of glucose, 4.0 g of PEG-400 and 12 mL of sulfuric acid solution were added again, fermentation was performed for 48 hrs at 33° C., and the above operations were cyclically performed thrice. The glucose conversion rate, the ethanol yield and the ethanol concentration are respectively as shown in FIGS. 12, 13 and 14. According to the data in the drawings, it can be seen that, when the PEG-400 was added into the fermentation system, the recovery efficiency of the yeast was very high and the ethanol concentration of 118 g·L$^{-1}$ could be achieved at the first time of recycling the recovered yeast after fermentation for 48 hrs.

Figure 15:
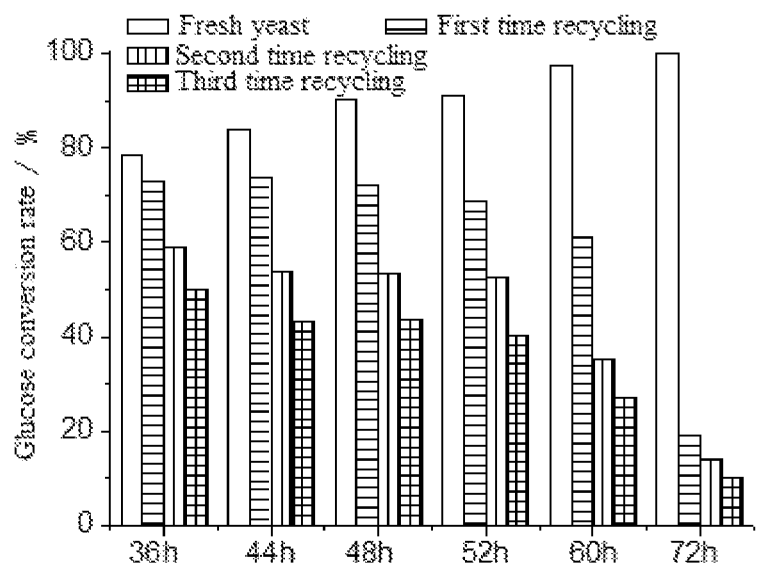
FIG. 15 illustrates the influences of a circulation of yeast fermented for 36-72 hrs in surfactant/water on glucose conversion rate.
Figure 16:
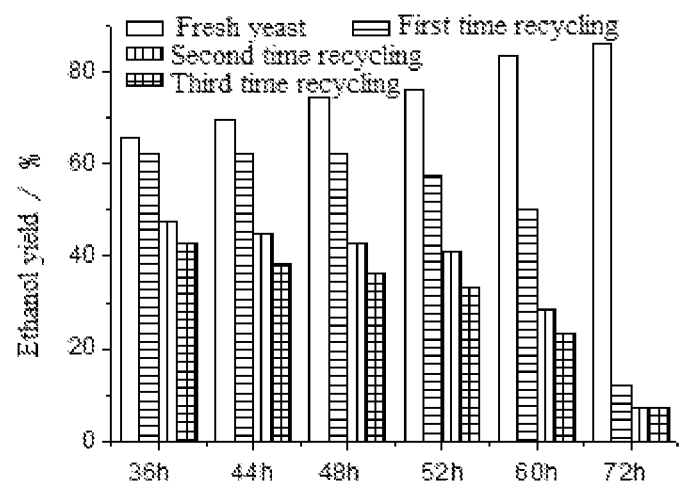
FIG. 16 illustrates the influences of a circulation of yeast fermented for 36-72 hrs in surfactant/water on ethanol yield.
Figure 17:
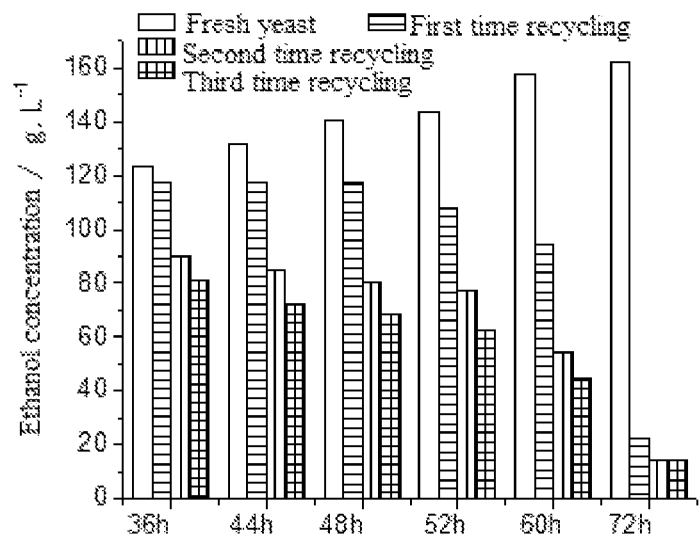
FIG. 17 illustrates the influences of a circulation of yeast fermented for 36-72 hrs in surfactant/water on ethanol concentration.

Example 30 Recycling of Yeast Fermented for 36-72 Hrs in Surfactant-Water Mixture System 0.5 g of yeast powder was rehydrated for 15-30 min at 25-38° C. by using 4 mL of ultrapure water, then 6.5 g of glucose, 4.0 g of PEG-400 and 12 mL of pre-prepared sulfuric acid solution with pH=4.3 were added, put in a shaker for shaking and fermentation was performed for 36-72 hrs at 33° C. After fermentation, refrigerated centrifugal separation at 8000 rpm was performed for 5 min, the supernatant was removed from the fermentation liquid after fermentation, solid yeast powder was left, 4 mL of ultrapure water, 6.5 g of glucose, 4.0 g of PEG-400 and 12 mL of sulfuric acid solution were added again, fermentation was performed for 48 hrs at 33° C., and the above operations were cyclically performed thrice. The glucose conversion rate, the ethanol yield and the ethanol concentration are respectively as shown in FIGS. 15, 16 and 17. According to the data in the drawings, it can be seen that, when the PEG-400 was added into the fermentation system, the recovery efficiency of the yeast was very high and the ethanol concentration of 118 g·L$^{-1}$ could be achieved at the first time of recycling the recovered yeast after fermentation for 48 hrs.

Figure 18:
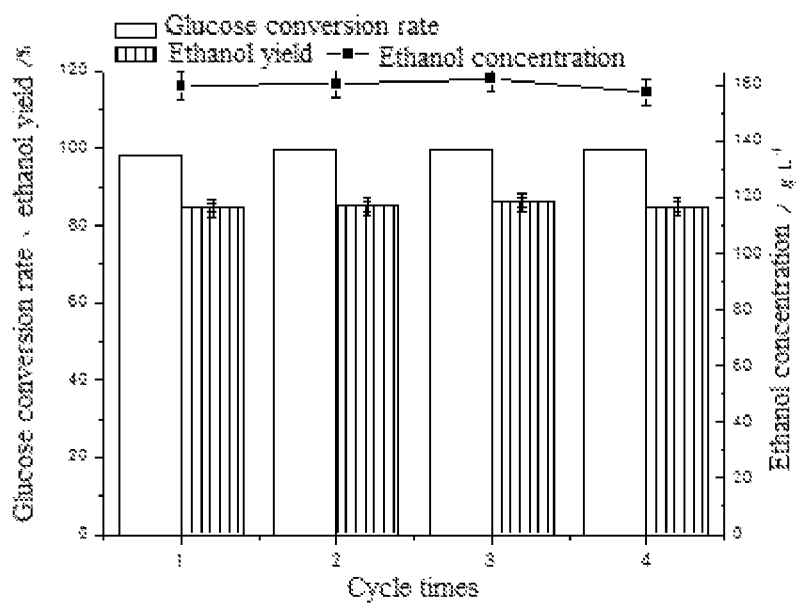
FIG. 18 illustrates recycling of surfactant/sulfuric acid.

Example 31 Recycling of Surfactant 0.5 g of yeast powder was rehydrated for 15-30 min at 25-38° C. by using 4 mL of ultrapure water, then 7.5 g of glucose, 4.0 g of PEG-400 and 12 mL of pre-prepared sulfuric acid solution with pH of 4.3 were added, then and put in a shaker for shaking and fermentation was performed for 72 hrs at 33° C. After fermentation, refrigerated centrifugal separation at 8000 rpm was performed for 5 min, solid yeast powder was removed, the supernatant was distilled, the residue obtained after distillation entered a next fermentation process, 0.5 g of yeast powder was added again and rehydrated for 15-30 min at 25-38° C. by using 4 mL of ultrapure water, 6.5 g of glucose and 12 mL of sulfuric acid solution were added again, fermentation was performed for 72 hrs at 33° C., and the above operations were cyclically performed for four times. The glucose conversion rate, the ethanol yield and the ethanol concentration are as shown in FIG. 18, the surfactant PEG-400 can be recycled and the fermentation efficiency is not influenced obviously.

The invention claimed is:
1. A surfactant-improved ethanol fermentation method comprising:
  forming a fermentation medium consisting of fermentable carbohydrate, a surfactant-water mixture, yeast cells, and a pH adjusting agent, wherein the yeast cells are *Saccharomyces cerevisiae* cells;
  and
  subjecting the fermentation medium to fermentation for producing ethanol;
  wherein the surfactant is a nonionic surfactant with one of the following formulae:

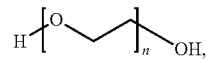

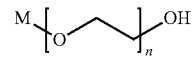

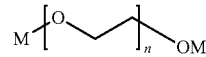

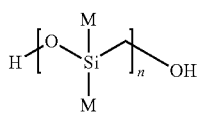

wherein n is 1-25, and M is methyl in these formulae.

2. The surfactant-improved ethanol fermentation method according to claim 1, wherein the fermentable carbohydrate is glucose and the concentration of the fermentable carbohydrate is 270-500 g/L.

3. The surfactant-improved ethanol fermentation method according to claim 1, wherein a mass ratio of the surfactant to water in the fermentation medium is 0.001-0.5.

4. The surfactant-improved ethanol fermentation method according to claim 3, wherein the mass ratio of the surfactant to water in the fermentation medium is 0.125-0.375.

5. The surfactant-improved ethanol fermentation method according to claim 1, wherein the resultant concentration of the *Saccharomyces cerevisiae* cells in the medium is $10^7$-$10^9$/L.

6. The surfactant-improved ethanol fermentation method according to claim 1 further comprising subjecting the fermentation medium to refrigerated centrifugation to recover the yeast cells, and applying the recovered yeast cells in a next fermentation process.

7. The surfactant-improved ethanol fermentation method according to claim 6 further comprising conducting the refrigerated centrifugation at a centrifugation speed of 4000-15000 rpm for 1-30 minutes.

8. The surfactant-improved ethanol fermentation method according to claim 1 further comprising performing refrigerated centrifugation to remove yeast, distilling the resultant supernatant to obtain residue comprising the pH adjusting agent and the surfactant, and applying the resultant residue in a next fermentation process.

9. The surfactant-improved ethanol fermentation method according to claim 8, wherein the distilling is conducted under a pressure of 0-0.09 Mpa, at a distillation temperature of 40-100° C., for 20-120 minutes.

10. The surfactant-improved ethanol fermentation method according to claim 8, wherein distilling is conducted in vacuum, and the fermentable carbohydrate, deionized water, and the resultant residue comprising the recovered surfactant and the pH adjusting agent are directly added in the next fermentation process during which the pH value of the fermentation medium is not re-adjusted.

11. The surfactant-improved ethanol fermentation method according to claim 1 further comprising synchronously recycling the yeast cells and the surfactant by recovering the yeast cells through refrigerated centrifugation, distilling the resultant supernatant to recover the surfactant, and applying the recovered yeast cells and the recovered surfactant simultaneously in a next batch of fermentation process.

12. The surfactant-improved ethanol fermentation method according to claim 1, wherein the fermentation temperature is 28-44° C.

13. The surfactant-improved ethanol fermentation method according to claim 12, wherein the fermentation temperature is 33° C.

14. The surfactant-improved ethanol fermentation method according to claim 1, wherein the fermentation time is 12-120 hrs.

15. The surfactant-improved ethanol fermentation method according to claim 14, wherein the fermentation time is 60 hrs.

16. The surfactant-improved ethanol fermentation method according to claim 1, wherein the pH of the fermentation medium is 3.0-6.5.

17. The surfactant-improved ethanol fermentation method according to claim 1, wherein the pH adjusting agent for the fermentation medium is one of sulfuric acid solution, citric acid-sodium citrate buffer solution, phosphoric acid buffer solution, carbonate buffer solution and acetic acid-sodium acetate buffer solution.

* * * * *